(12) United States Patent
Andle

(10) Patent No.: US 7,181,957 B2
(45) Date of Patent: Feb. 27, 2007

(54) MEASUREMENT, COMPENSATION AND CONTROL OF EQUIVALENT SHEAR RATE IN ACOUSTIC WAVE SENSORS

(75) Inventor: Jeffrey C. Andle, Brewer, ME (US)

(73) Assignee: Biode Inc, Westbrook, ME (US)

( * ) Notice: Subject to any disclaimer, the term of this patent is extended or adjusted under 35 U.S.C. 154(b) by 0 days.

(21) Appl. No.: 11/313,029

(22) Filed: Dec. 19, 2005

(65) Prior Publication Data

US 2006/0096357 A1    May 11, 2006

Related U.S. Application Data

(62) Division of application No. 10/743,986, filed on Dec. 22, 2003, now Pat. No. 7,007,546.

(51) Int. Cl.
*G01N 11/10* (2006.01)
(52) U.S. Cl. .................... 73/54.41; 73/54.01; 73/54.24
(58) Field of Classification Search ............... 73/54.01, 73/54.23, 54.24, 54.25, 54.41
See application file for complete search history.

(56) References Cited

U.S. PATENT DOCUMENTS

| | | | |
|---|---|---|---|
| 3,712,117 A | 1/1973 | Fitzgerald et al. | |
| 3,903,732 A | 9/1975 | Rork et al. | |
| 5,235,235 A | 8/1993 | Martin et al. | |
| 5,750,884 A | 5/1998 | Field | |
| 5,877,411 A | 3/1999 | Namerikawa et al. | |
| 6,260,408 B1 | 7/2001 | Vig et al. | |
| 6,357,281 B1 | 3/2002 | Wilhelm | |
| 6,439,034 B1 | 8/2002 | Farone et al. | |
| 6,543,274 B1 | 4/2003 | Herrmann et al. | |
| 2002/0124634 A1 | 9/2002 | Litton | |
| 2005/0132784 A1 | 6/2005 | Andle | |

*Primary Examiner*—Daniel S. Larkin
(74) *Attorney, Agent, or Firm*—Shalom Wertsberger; Saltamar Innovations

(57) ABSTRACT

A method for controlling the shear rate at which an acoustic wave device measures viscosity by calculating the shear rate as a function of the characteristic rate of quartz movement in response to a given input transducer power level and the viscosity of the fluid and then by adjusting the input transducer power level to obtain the desired shear rate for the viscosity measurement by optimizing the power level. Related aspects of the invention provide for methods for characterizing viscoelastic fluids at a plurality of predetermined shear rates using a plurality of optimized power levels, a plurality of sensor designs, or a plurality of both optimized power levels and sensor designs.

17 Claims, 4 Drawing Sheets

US 7,181,957 B2

MEASUREMENT, COMPENSATION AND CONTROL OF EQUIVALENT SHEAR RATE IN ACOUSTIC WAVE SENSORS

RELATED APPLICATIONS

This application is a divisional application of, and claims priority from, U.S. patent application Ser. No. 10/743,986 filed Dec. 22, 2003, presently U.S. Pat. No. 7,007,546.

FIELD OF THE INVENTION

This application is directed generally to acoustic wave sensors employing sound waves to measure viscoelastic properties of a material, and more particularly to methods of relating viscosity measurements to the shear rate at which such measurements are performed.

BACKGROUND OF THE INVENTION

Viscosity, and more generally, viscoelasticity, are properties of liquids and solids that relate the shear forces generated by or applied to a material to the amount of shear deformation or flow. While the invention applies equally well to viscoelasticity, the present discussion will be limited to viscosity measurement for simplicity. Viscosity is of widespread interest in many manufacturing environments and is measured as a primary quality of some products and as a secondary quality (a means of monitoring process state) in other processes.

Viscosity describes the force required in order to make successive molecular layers of a liquid move past each other at a given rate of shear ("shear rate"). If one considers a liquid flowing past the walls of a container, the liquid will ideally have no motion relative to the wall at the interface and will have increasingly higher velocities as one observes points successively further from the wall. The shear rate is defined as the gradient of the velocity of the liquid parallel to the surface (meters per second) with increasing distance from the surface (meters). The units of shear rate are 1/seconds. The shear stress is the amount of force per unit area that must be applied in order to cause the motion. While the fluid may have a characteristic flow (and thus a characteristic shear rate) or may be stationary, all measurements of viscosity to date are based on the measurement of shear stress vs. shear rate under an imposed motion of the fluid. Throughout this disclosure, "shear rate at which the viscosity of a fluid" should be taken to mean the shear rate at which the viscosity of the fluid is measured, which may differ substantially from the characteristic shear rate of the fluid in its intended application or point of measurement.

Intrinsic viscosity is defined as the ratio of the shear stress to the shear rate and has units of pressure (force per unit area) times seconds, or Pascal-seconds. Intrinsic viscosity is typically measured using a rotating cylinder of known diameter at a controlled rate of rotation concentric within another stationary cylinder. Knowledge of the torque on the rotating cylinder and its rate of rotation, along with geometrical factors, allows one to measure the intrinsic viscosity, or simply the "viscosity", $\eta$.

While this method is widely used and highly accurate, it is difficult to successfully apply to process control or to operate on moving platforms. The ability to accurately measure nonlinearities of viscosity as a function of rotational rate notwithstanding, the use of moving parts limits utility and reliability. The requisite sample sizes and difficulty in setting up and cleaning up a measurement motivate other alternatives.

Hydrodynamic properties of liquids are quantified by the speed of shear sound-waves in a liquid. An ideal liquid, having neither shear elasticity nor viscosity, cannot support a shear sound wave. An elastic solid having a shear stiffness, $\mu$, can support a shear acoustic wave that propagates through the solid much as the better known compressional sound wave. Viscous liquids can support a shear sound wave; however the wave decays as it travels and is only able to travel a few wavelengths before being totally damped out by frictional losses. Nonetheless, these "sound waves" are related to the flow of liquids in confined geometries, such as capillaries, pipes and the spaces between moving parts in machinery. These flows are governed by the ratio of the intrinsic viscosity, a, to the density of the material, p. The ratio is known as the "kinematic viscosity", $\eta_k = \eta/\rho$, and has the units of area over time (m²/s).

Kinematic viscosity is typically measured using a controlled glass capillary tube maintained in a water bath with a reproducible force (gravity, air pressure, or vacuum) applied. The velocity of a sample through the capillary is measured. The "shear rate" is a function of the speed of the sample and the geometry of the capillary. While this method enjoys widespread use and there exist numerous clever methods of automating sample injection and measurement, the approach is not without its problems and the industry is in need of alternative solutions. A principal problem with this method is the discontinuous and sampled nature of the measurement, in which it is typically performed off-line in a laboratory separate from the process being monitored and controlled. Other drawbacks are the size of the apparatus and its susceptibility to vibration and orientation of the capillary.

Acoustic waves offer an attractive method of measuring the viscoelastic properties of liquids and solids, including oils, paints, inks, polymers and glasses. Prior art has indicated a number of methods by which viscosity is measured, as well as methods in which a change in viscosity is used as an indication of a chemical measurement. While the invention is equally applicable to either scenario, the disclosure will focus on the measurement of viscosity itself.

The propagation of shear acoustic waves in a liquid, while difficult to instrument reliably, offers a direct measurement of the kinematic viscosity. The square of the phase velocity of the wave in the liquid divided by the radian frequency of the wave, $\omega$, is a direct measure of $\eta_k$. The method is not employed due to the substantial variations in the size of a wavelength with changes in viscosity and the significant signal to noise ratio issues associated with measuring the phase velocity of a heavily damped wave over a small number of acoustic wavelengths.

The compressional wave amplitude and velocity are a weak function of the shear viscosity. Assuming that the compressional stiffness constant, $\lambda$, has no loss of its own (elastically compressible liquid), the effective elastic modulus of the compressional plane wave is $\lambda + 2j\omega\eta$, where j is the complex operator and $\omega$ is the radian frequency. Assuming $\omega\eta << \lambda$, the viscoelasticity is a weak and approximately linear function of the viscosity. The square of the compressional wave velocity may be expressed as the ratio of the effective elastic modulus to the density. Measurements of the compressional wave velocity are often correlated to the viscosity by assuming that the compressional modulus, $\lambda$, and the density, $\rho$, are unchanged. These quantities are not typically invariant and therefore the results of measurements described in the like of U.S. Pat. No. 6,439,034 to Farone et al. are inaccurate; however this method is applied to process control as an approximation. At present there is no meaningful definition or measurement of shear rate in this method and the method is typically recommended only for Newtonian liquids, that is liquids in which the viscosity is independent of the shear rate and is constant. The method suffers constraints of fixed geometry between the transducers that sometimes does not fit the flow requirements within a process, and as the Farone et al. patent discloses only measurement of the phase difference between the longitudinal and shear wave without consideration of the amplitude or attenuation of the wave, it suffers from operating under certain meaningful, but unknown operating conditions, such as the signal amplitude, which are known to change the measured quantity. This limitation is specifically important in liquids that exhibit non-linear viscosity response to shear rate.

In addition to the propagation of acoustic waves through a material, it is possible to employ acoustic waves in an adjacent solid to measure the power transfer into the viscous liquid. Power transfer from one medium to the other is governed by the ratio of the acoustic impedances of the materials and is well known to one skilled in the art. Power transfer of acoustic energy between a solid waveguide and an adjacent liquid forms the basis of several viscometers. The rate of energy transfer (power loss) is dependent on the relative acoustic impedances of the waveguide material and the adjacent liquid in a manner well-known to one skilled in the art. The acoustic impedance of the shear wave in the solid waveguide is the square root of the product of the density, $\rho$, and the shear elastic stiffness, $\mu$. It is predominantly real (resistive) and is analogous to a nearly-lossless transmission line's characteristic impedance in electromagnetics. The acoustic impedance of a shear wave in a viscous liquid is the square root of the product of the stiffness term, $j\omega\eta$, with the density, $\rho$. The characteristic impedance of the viscous liquid is typically very small compared to the elastic solid, resulting in a low power transfer. At low viscosity the power transfer is proportional to $(\omega\rho\eta,)^{1/2}$.

One method of performing this measurement is to immerse a resonator, typically a disc of quartz crystal of AT cut, into the liquid and to measure the shift in resonant frequency or loss at resonance. This method has been plagued by poor reproducibility when used with affordable instrumentation, primarily due to the lack of a differential measurement.

In all of the acoustic wave methods, it has generally been virtually impossible to correlate the "shear rate" at which the measurement occurs to the "shear rate" of such reference methods as the rotating spindle or the capillary tube. Therefore, while the acoustic wave methods are structurally superior, having no moving parts and offering continuous in situ measurement, they are not widely accepted due to the unknown conditions under which the measurements occur.

Ideally the viscosity of a liquid is a constant property that is independent of the rate of shear. That is, the stress is a linear function of the shear rate and the slope of the stress vs. shear rate, or "viscosity", measured by one instrument type or at one shear rate would be identical to that measured by another instrument type or at another shear rate. This is, unfortunately not the case, and all liquids exhibit nonlinearity beyond a given stress limit or shear rate limit. There are a wide variety of mechanisms for the observed nonlinearities and a correspondingly large number of models to describe the effect.

A common model for liquid is known as the Maxwellian model, in which the liquid is assumed to have a fixed stiffness in parallel with viscosity, so that the Maxwellian liquid behaves as a semi solid beyond a given shear rate. This model is widely adapted in the field of acoustic sensors because it quickly lends itself to the analysis of harmonic motion such as in waves. In the Maxwellian model it is assumed that the stiffness constant, $\mu$, and the viscosity, $\eta$, are both constant and that the properties of the material are linear with changes in the amplitude of the acoustic wave, varying only with changes in the frequency of the motion. While many liquids exhibit behaviors consistent with this model at relatively low frequencies and amplitudes, this has been found to be an erroneous assumption in general. The most significant error to result from this assumption is to equate the shear rate of the sensor with the frequency of the harmonic motion. Thus, one sees sensors based on 10 MHz quartz crystals described as $10^7$ 1/seconds shear rate viscometers, when in fact, they exhibit unknown and uncontrolled shear rates on the order of $10^2$ to $10^5$ 1/seconds, depending on the acoustic amplitude and other geometric factors.

The preferred embodiment of the present invention has been analyzed and was found to have an uncontrolled shear rate of between $10^3$ and $2\times10^7$ 1/seconds. The shear rate is a function of several factors, most notably the power level of the acoustic wave transmitted into the sensor and the viscosity of the liquid being measured.

In U.S. Pat. No. 39,903,732 to Rork et al., a sensor is provided in which a transducer therein provides an energy transduction from one form of energy to another and in doing so has surfaces of the transducer placed in motion in directions such that shear wave energy is imparted to those portions of the fluid of interest adjacent to those surfaces. The transducer has electrical input terminals to which oscillator circuitry is attached whereby the circuit oscillation frequency is a resonant frequency associated with the moving surfaces when submerged in a fluid. Rork acknowledge a dependence of a material's viscosity on the magnitude of the applied stress, and further states that "This sensor measures the point fluid viscosity of non-Newtonian fluids for the particular shear stress applied." Rork then discuss a means to potentially control the stress. The predominant practice in the fields of viscometry and rheology is to measure viscosity as a function of shear rate and not of stress. This practice is addressed by the present invention which, in its various aspects, measures, controls and varies the shear rate of the sensor as opposed to the peak stress of the transducer. Furthermore, the present invention allows a correlation of the shear rate to mechanical viscometers such as the Brookfield™ (Brookfield Inc. Middleboro, Mass. U.S.A. ) viscometer which is considered the standard measurement device for this purpose.

Therefore a promising class of sensors for measuring viscosity or for measuring chemical processes that induce a change in viscosity are underutilized by the industry, primarily because those sensors do not provide for measurement or control of the shear rate at which the viscosity is being measured. It is further found that this class of sensors are being underutilized because it is not presently possible to maintain a constant shear rate in the sensor over a range of viscosities or to reproducibly alter the shear rate of the measurement over a desired range in a given sample. It is an object of the present invention to overcome various aspects of the limitations described above. It is a further object of the invention to provide for measurement of viscosity at a controlled shear rate, preferably representative of the intended application.

SUMMARY OF THE INVENTION

An important aspect of the invention is a method for measuring the shear rate at which a viscosity measurement is carried out. However the invention further provides a method for controlling the shear rate in which such viscosity measurements are conducted. Various uses of those two capabilities provides several other methods and uses to which the invention further extends.

The preferred embodiment of the present invention utilizes propagation of acoustic energy along an acoustic waveguide (rod or plate) and measuring the power dissipation into the liquid by comparing the input and output power levels. This method has been successfully implemented using a multi-reflective delay line, (as described by U.S. Pat. No. 7,002,281, to the present inventor; the application is hereby incorporated by reference in its entirety), but is equally applicable to other acoustic wave devices.

It is therefore an aspect of the present invention to provide a method for measuring shear rate at which the viscosity of a fluid is being measured utilizing an acoustic wave device, the acoustic wave device having an input and an output transducers, and having a characteristic relationship between input power, output power, and an acoustic wave amplitude at a selected region between the input and output transducer, the acoustic wave device being coupled to the measured fluid, the method comprising the steps of:
  applying a predetermined power $P_{in}$ of a harmonic signal having a frequency $\omega$ to the input transducer, to impart an acoustic wave at the selected region;
  measuring output power level $P_{out}$ at the output transducer;
  using the characteristic relationship, and the input and output power levels, calculating the amplitude of the average acoustic wave imparted to the fluid;
  measuring viscosity of the fluid to obtain a measured viscosity at the selected region; and
  calculating the shear rate of the fluid at the selected region by using the frequency, the viscosity measurement, and the acoustic wave amplitude.

In the preferred embodiment the step of measuring viscosity is performed utilizing the acoustic wave device, and more preferably by calculating power insertion loss between the input and output transducers, or calculating what is known as the change in 'acoustic impedance' of the transducer. In the preferred embodiments, the selected region above contains therewith the geometrical midpoint between the input transducer and output transducer respective geometries.

In other embodiments, the step of measuring viscosity is carried out by measuring phase shift of the imparted signal or measuring the frequency change required for maintaining a constant phase shift of the imparted signal.

In the preferred embodiment, the step of calculating the shear rate is carried out by utilizing the formula for penetration depth of the acoustic wave into the fluid, $\delta=\sqrt{2\eta/\omega\rho}$, where $\omega$ is the radian frequency of the applied harmonic wave having frequency, F, and $\omega=2\pi F$, $\rho$ is the density of the sample liquid, and $\eta$ is the intrinsic viscosity (Pascalseconds); utilizing a design parameter 'C' of the acoustic wave device, to relate the wave displacement 'U', to the average power flow, Pavg, as $U=C\sqrt{P_{avg}}$; and utilizing the frequency of the imparted signal and the foregoing calculations of the penetration depth and the displacement of the crystal face U, to calculated the shear rate as $\dot{\gamma}=\omega U/\delta$.

Furthermore, a method is provided for measuring shear rate at which the viscosity of a fluid is measured, wherein the step of calculating the shear rate is carried out to produce a correlation between the amplitude and the geometric average of the power inserted at the input power and the power sensed at the output transducer.

The preferred embodiments further comprise measuring the fluid temperature, and the density of the fluid, however assumptions may be used for those parameters.

In a second aspect of the present invention, there is provided a method for measuring viscosity of fluid at a desired shear rate, utilizing an acoustic wave device having an input and an output transducers, and having a known relationship between input power, output power, and an acoustic wave amplitude at a selected region between the input and output transducer, the acoustic wave device being coupled to the measured fluid, the method comprising the steps of:
  a. selecting an initial input power level, as an estimated power level;
  b. applying a harmonic signal having the estimated power level to the input transducer, to impart an acoustic wave of pre-selected amplitude at the selected region;
  c. using the acoustic wave device, measuring viscosity of the fluid to obtain a measured viscosity at the selected region;
  d. calculating the actual shear rate of the fluid at the selected region by using the viscosity measurements, and the acoustic wave amplitude;
  e. calculating the difference between the actual shear rate and the desired shear rate to produce a shear rate error;
  f. adjusting the estimated input power level to compensate for the shear rate error; and
  g. using the adjusted estimated power level, repeating the steps iii through vi until the shear error rate is within acceptable tolerance from the desired shear rate.

In the preferred embodiment, the step of selecting further comprises the step of estimating the input power level required to impart the desired shear rate to the fluid, and using the estimated power level in the step of applying. More preferably, the step of estimating utilizes information relating to the fluid to be measure for estimating the output power at the output transducer. However, the estimated power level may be selected randomly, or for example selected to be about the mid point of the power range applicable to the acoustic wave device.

Similar to other aspects of the invention, in the preferred embodiment the step of measuring the viscosity is carried out by calculating power insertion loss between the input and output transducers, however other methods, mentioned above or otherwise commonly known, may be utilized under the invention.

The mathematical steps described for calculating the shear rate above are applicable to the preferable embodiment of this aspect of the invention.

The step of adjusting the input power level may be carried out by any desired algorithm. In one preferred embodiment, the step of adjusting is carried out utilizing a PID algorithm.

In yet another aspect of the invention, there is also provided a method for characterizing viscoelastic properties of a fluid by utilizing an acoustic wave device coupled to the fluid, the device having an input and output transducers, the method comprising the steps of selecting a set of input power levels in accordance within a range of input power levels appropriate to the acoustic wave device, and for each of the selected input power levels:
  i. applying the selected input power level to the input transducer;
  ii. measuring an output signal from the output transducer;

iii. calculating the viscosity of the fluid utilizing the applied input power level and the measured output signal; and iv. calculating the shear rate at which the viscosity measurement occurred, utilizing the applied input power level and the measured output signal.

Most preferably, the input power levels represent a continuum. The mathematical steps described for other aspects of the invention for calculating the shear rate are applicable to this aspect as well.

Yet another aspect of the invention, comprises a method for characterizing viscoelastic properties of a fluid by utilizing an acoustic wave device coupled to the fluid, the device having an input and output transducers, the method comprising the steps of selecting a set of desired shear rates for measuring the fluid viscosity, and for each of the selected desired shear rates:

a. selecting an estimated input power level;

b. applying the estimated input power level to the input transducer;

c. measuring an output signal from the output transducer;

d. calculating the viscosity of the fluid utilizing the applied input power level and the measured output signal;

e. calculating the actual shear rate at which the viscosity measurement occurred, utilizing the applied input power level and the measured output signal;

f. calculating the difference between the actual shear rate and the desired shear rate to produce a shear rate error;

g. adjusting the estimated input power level to compensate for the shear rate error; and h. using the adjusted estimated power level, repeating the steps b through g until the shear rate error is within acceptable tolerance from the desired shear rate.

In yet another aspect of the invention, there is provided a method for measuring shear rate at which the viscosity of a fluid is being measured utilizing a single port acoustic wave device having a characteristic relationship between input power and an acoustic wave amplitude, the acoustic wave device having a crystal with at least one face coupled to the fluid to impart an acoustic wave thereto, and having a known relationship between applied power and displacement U of the crystal face, the method comprising the steps of:

applying harmonic energy signal having a frequency ω to the acoustic device;

measuring the input power level of harmonic energy signal;

using the characteristic relationship, and the input level, calculating the amplitude of the average acoustic wave imparted to the fluid;

measuring viscosity of the fluid in the vicinity of the acoustic wave device, to obtain a measured viscosity δ; and calculating the shear rate of the fluid $\dot{\gamma}$ at which the by using the frequency, the viscosity measurement, and the displacement of the crystal face.

The step of calculating preferably comprises using the formula $\dot{\gamma}=\omega U/\delta$. The step of measuring viscosity may be performed using a phase shift of the harmonic energy signal, using an impedance measurement of the acoustic wave device, by adjusting the frequency of the harmonic signal, or by any other convenient method.

It is another aspect of the invention, to provide a method for measuring shear rate at which the viscosity of a fluid is being measured utilizing a single port acoustic wave device having a characteristic relationship between input power and an acoustic wave amplitude, the acoustic wave device having a crystal with at least one face coupled to the fluid to impart an acoustic wave thereto, and having a known relationship between applied power and displacement U of the crystal face, the method comprising the steps of:

feeding harmonic incident signal of frequency ω to an incident port of a directional coupler and measuring the power of the incident signal;

coupling a transmission port of the directional coupler to a single port transducer, the transducer being coupled to the fluid to be measured;

measuring reflected power at a reflection port of the directional coupler;

deriving an acoustic wave device input impedance from the measured incident power and the measured reflected power;

calculating the fluid viscosity δ utilizing the input impedance; and calculating the shear rate of the fluid $\dot{\gamma}$ at which the by using the frequency, the viscosity measurement, and the displacement of the crystal face.

Preferably, the step of calculating comprises using the formula $\dot{\gamma}=\omega U/\delta$.

The invention also provides for an apparatus for measuring shear rate at which the viscosity of a fluid is being measured, the apparatus comprising a single port acoustic wave device coupled to the liquid having a known relationship between harmonic power signal applied thereto and a displacement of a crystal face of the acoustic wave device in response to the applied power. A driving circuitry adapted to provide the harmonic signal power has an incident wave power detector coupled to the driving circuitry. A directional coupler comprising an incident port, a reflection port, and a transmission port, coupled to the acoustic device, and a reflected wave power detector coupled to the reflection port. The incident port is being coupled to the driving circuitry and the incident power detector.

In such an apparatus for measuring shear rate, the step of calculating preferably comprises using the formula $\dot{\gamma}=\omega U/\delta$.

SHORT DESCRIPTION OF DRAWINGS

The invention will be better understood with the aid of the enclosed drawings in which.

DETAILED DESCRIPTION

Figure 1:
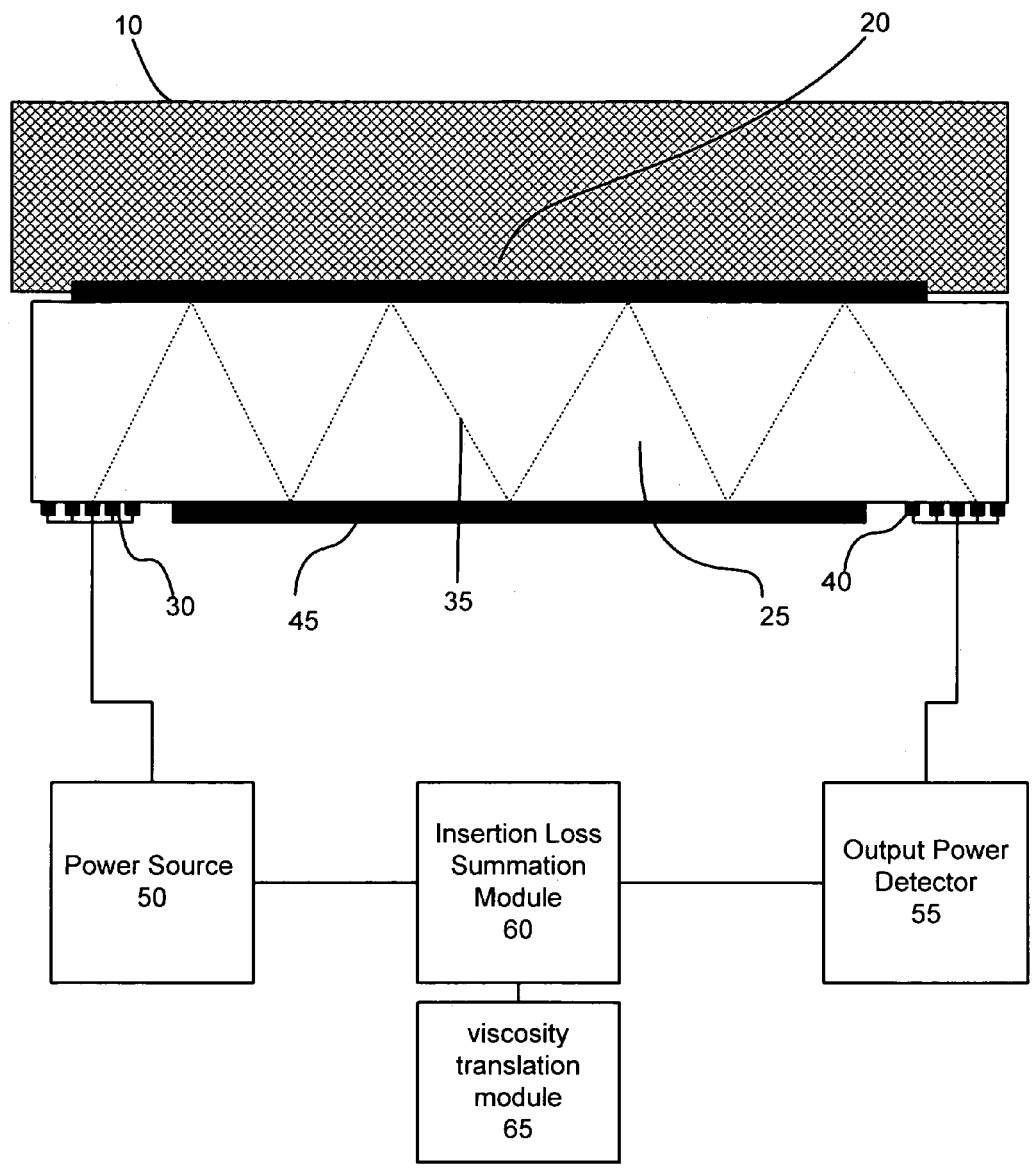
FIG. 1 depicts a simplified diagram of an acoustic wave device interacting with a fluid, including drive and other electronics, in accordance with the preferred embodiment of the invention.

In these specifications, an acoustic wave device is considered a device comprising a crystalline material having a plurality of electrodes, and that in response to electrical power presented between at least a pair of these electrodes, provides a corresponding movement of the crystal face, and conversely, generates an electrical signal in the electrodes in response to power applied to the crystal face.

The preferred embodiment utilizes a known method for viscosity measurement, comprising an acoustic wave device 45 comprising a piezoelectric crystal 25, with an input transducer 30 and an output transducer 40 coupled to it. The input transducer is coupled to a power source 50, which injects a harmonic signal of known power level and frequency. The energy coupled to the input transducer causes an acoustic wave 35 to travel in the crystal, and impart a wave to the fluid 10. Since energy is transferred to the fluid 10, the level of power that arrives at the output transducer 40 is lower than the input power. The difference therebetween is referred to as insertion loss. The insertion loss is representative of the acoustic impedance imparted by the fluid, and is representative of the fluid viscosity. The output level is measured by an output power detector 55, and the measurement results are transferred to an insertion loss summation module 60 that may be implemented by hardware or software. The insertion loss summation is transferred to a viscosity translation module 65, typically a numerical computer, a display device, a process controller, and the like.

For a known acoustic device design, those skilled in the art can deduct, either computationally or empirically, a displacement of the crystal face responsive to the power absorbed by the device, as represented by the input and output power. The displacement of the crystal face may vary throughout the device, but an average displacement can generally be computed for a region representing the geometrical midpoint between the input and output transducers. Other points may be selected and the selection of region is a matter of engineering choice.

If a fluid is in contact with the crystal face, the crystal face displacement imparts a shear wave to the fluid which it contacts. The shear wave travels a distance into the fluid but normally decays rapidly, at a rate related to the viscosity, density, temperature and other characteristics of the fluid. The distance traveled by the wave before it decays below practical use level is referred to in these specifications as penetration depth $\delta$. Together with other parameters of the fluid, the shear rate caused by the wave may be calculated by first calculating the penetration depth $$\delta = \sqrt{2\eta/\omega\rho}$$

where, $\omega$ is the radian frequency of the applied harmonic wave having frequency, F, and $\omega = 2\pi F$, $\rho$ is the density of the sample liquid and $\eta$ is the intrinsic viscosity (Pascal-seconds).

The average power and measured viscosity thus provide an indication of the shear rate imposed upon the fluid in the selected region. Since, as described above, the same acoustic wave device may be used to measure the viscosity, one can provide an actual shear rate value at which the viscosity measurement took place.

As will be clear to those skilled in the art, certain parameters such as temperature (an important measurement condition) and density (needed to obtain shear rate and viscosity from power level measurements) may be assumed or measured. The preferred embodiment utilized separate measurements of the temperature and the density. The method of measurement is immaterial for the present invention. It is also clear that the crystal face does not need to actually contact the fluid, but that any stiff material may be used as an intermediary layer 20, provided the layer is compatible with and integrated into the design of the acoustic wave device.

Figure 2:
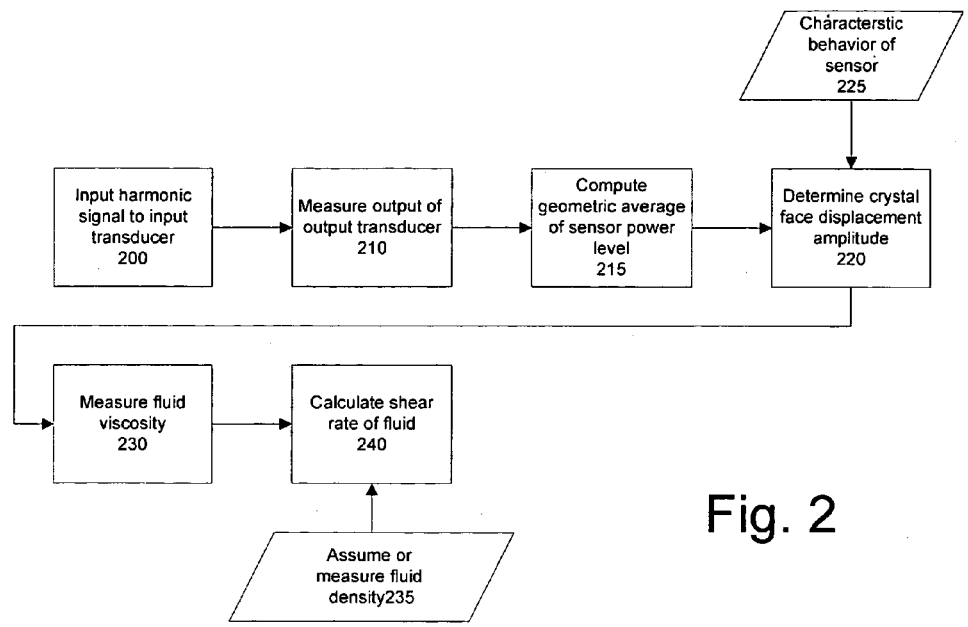
FIG. 2 depicts a simplified block diagram of a method for measuring the shear rate at which the viscosity of a fluid is measured.

Therefore, an aspect of the invention depicted in FIG. 2, provides for viscosity measurement together with the shear rate at which this measurement was performed, by utilizing an acoustic wave sensor device with known relationship 225 between the power dissipated therein and the amplitude U of the crystal face displacement. The sensor device is brought into contact with the fluid to be measured, either directly or indirectly. The input transducer 30 is fed 200 a harmonic signal at a known power level $P_{in}$, and the output of the output transducer $P_{out}$ 210 is measured. In the preferred embodiment, the geometric average of the power level ($P_{avg} = \sqrt{P_{in} * P_{out}}$), in watts of power transmission per unit cross-section of the sensor, is computed 215. The amplitude U of the crystal face displacement is found 220 from $P_{avg}$ and the characteristic behavior of the sensor 225. The acoustic amplitude, U, is then obtained from the average power flow per unit cross-section, $P_{avg}$ in Watts per unit area using a predetermined design constant, C, as $$U = C \cdot \sqrt{P_{avg}}.$$

A viscosity measurement is carried out 230 in one of several potential methods. In the preferred embodiment by the relationship between viscosity and decibel power insertion loss $P_{il}$ ($P_{il} = P_{in}(dB_{mW}) - P_{out}(dB_{mW})$) as disclosed in U.S. patent application Ser. No. 10/620,934, filed Jul. 16, 2003, already mentioned and incorporated above. Clearly, other methods for measuring viscosity are well known, and the method described in the above-mentioned application is merely the subject of engineering preference.

Utilizing either assumptions or measurements of the density of the fluid 235, and the foregoing measurements of the viscosity and the displacement of the crystal face U, the shear rate is calculated 240 as $$\dot{\gamma} = \omega U / \delta.$$

Several alternate methods of measuring viscosity utilizing an acoustic wave device are well known in the art, such as for example utilizing changes in a phase shift through a delay path, the frequency at which the phase is maintained at a constant value, or the impedance of a resonator device. Other methods are based, like the preferred embodiment, on measuring the impedance change of the transducer due to its interaction with the liquid. It will be clear that all those methods are equivalently suitable for the task as the preferred embodiment of measuring insertion loss. Similarly, while the preferred embodiment relates to viscosity measurements, and crystal face amplitude in a region in the vicinity of the geometrical center of the device, other regions may be selected as well, however the principle of the present invention is still equivalently applicable and the claims should not be limited to the preferred embodiment, but extend to such equivalent methods, too numerous to detail herein, but known to the one skilled in the art.

Figure 3:
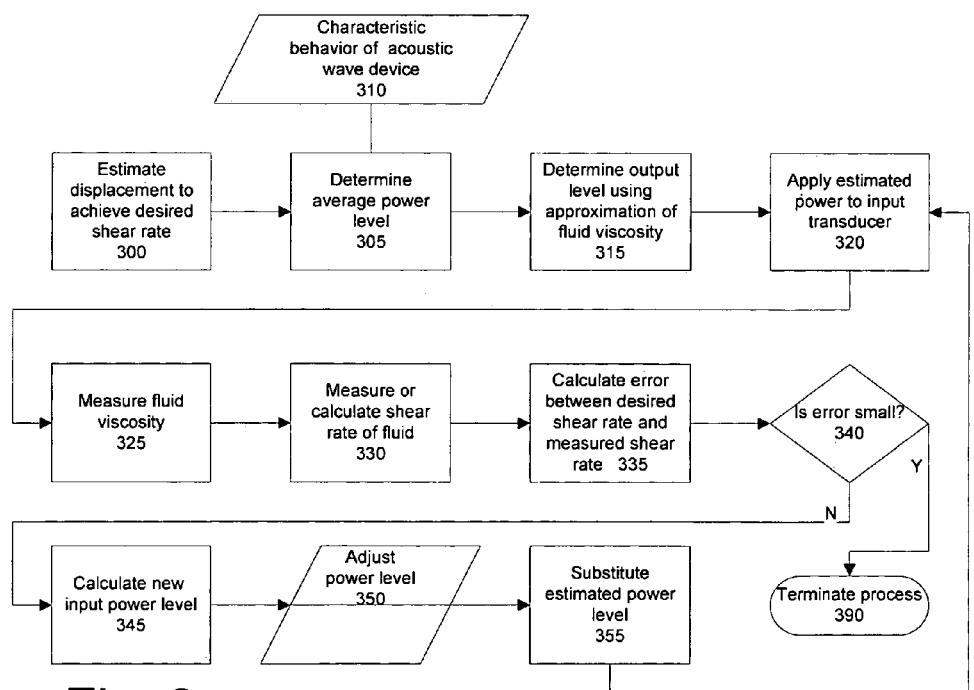
FIG. 3 depicts a simplified block diagram of a method for measuring fluid viscosity at a selected shear rate.

Another aspect of the invention, depicted in FIG. 3, calls for a measurement of viscosity at a predetermined shear rate. This is carried out by first estimating 300 the displacement U required to achieve the desired shear rate. The desired average power level is found 305 from the characteristic behavior of the acoustic wave device 310. Optionally, a further estimate 315 is performed for finding the output level using an approximation of the viscosity of the fluid, however any power level may be initially applied to the transducer, and the estimate is simply a method to minimize the hunting process for the appropriate power level. The estimated power is applied to the input transducer 320, and the viscosity is measured 325. A measurement and calculation of the shear rate is performed 330 as described above. The error between the desired shear rate and the measured shear rate is calculated 335. If the error is sufficiently small 340 for the desired measurement accuracy the process is terminated 390. Otherwise, a new, input power level is then calculated 345 to achieve an adjusted power level to compensate for the error. Such adjustment may be carried out by any one of well known algorithms such as halving the error, fully correcting for it, utilizing a PID (Proportional, Integral, Differential) based correction, and the like. The adjusted power level 350 is substituted 355 for the previously estimated power level and the process repeats until the error becomes sufficiently small to satisfy the requirements of the measurement. This aspect of the invention is especially applicable to in-process viscosity measurements, as successive viscosity measurement can be provided at a constant shear rate.

Figure 4:
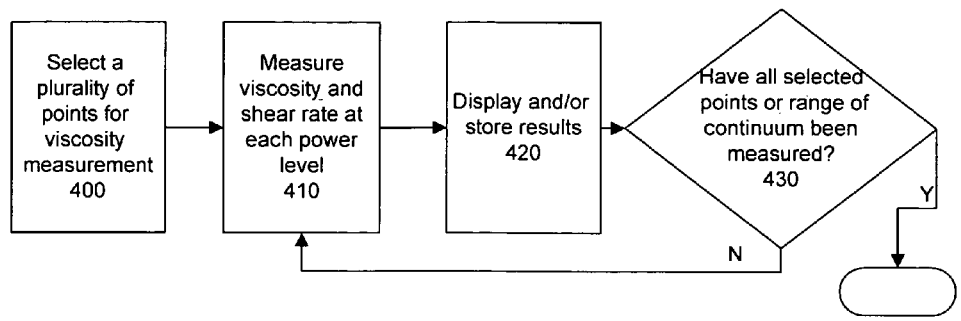
FIG. 4 depicts a simplified block diagram of a method for characterizing a fluid viscosity with respect to shear rate.

Yet another aspect of the invention, depicted in FIG. 4, allows for characterizing a fluid viscosity at a plurality of shear rates. Similar to the process described above, it will be clear that a plurality of power points may be selected and the viscosity measured at the shear rates tabulated. Thus, a plurality of $P_{in}$ points are selected 400 for viscosity measurement at a given shear rate. Such plurality may be selected randomly, or by other criteria such as, by way of example dividing the allowable power range according to some selected scale, such as logarithmic, linear, and the like. The points in the preferred embodiment represent a virtual continuum, to allow easy and detailed representation of the viscosity behavior with respect to varying shear rates. For each power level, a viscosity and shear rate measurement is performed 410, and the results are tabulated, graphed, displayed and/or otherwise stored 420, until all selected points, or the range of the continuum has been measured 430, at which point the process may be terminated 440. The advantage of selecting a continuum of selected input power levels is that it allows coverage of all possible shear rates that the acoustic wave device is practically capable of measuring without the need for the repetitive hunting steps described in FIG. 3.

If however a set of,specific shear rate and viscosity measurements are desired, the process described in FIG. 3 may be substituted, and the selected input power level points, or the calculation of the error between the desired shear rate and the measured shear rate is utilized to obtain the desired result set.

Figure 5:
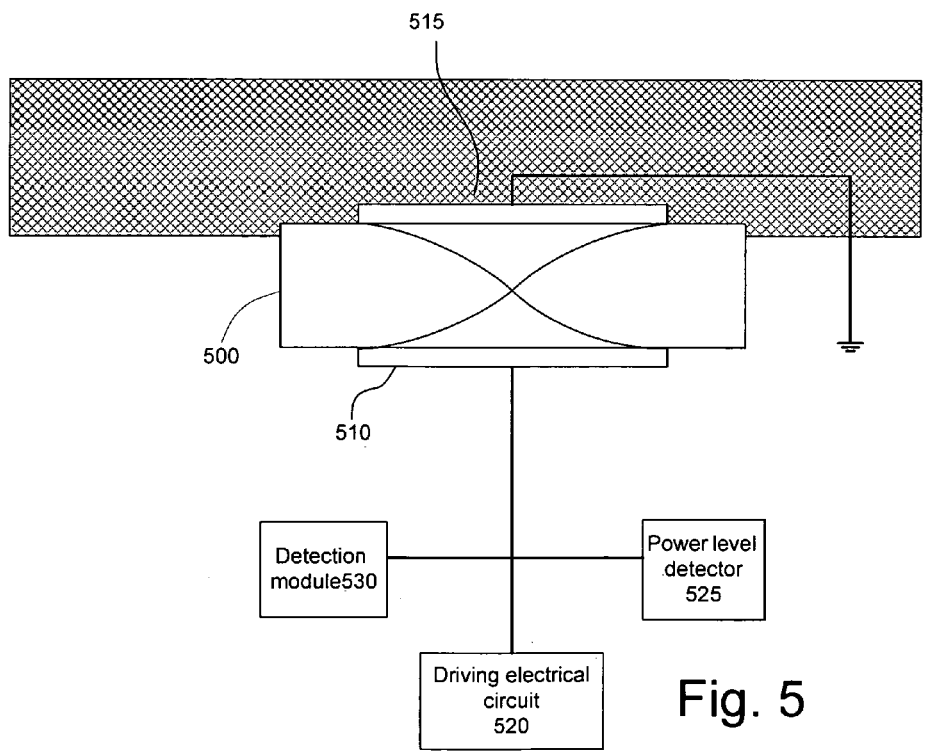
FIG. 5 depicts a simplified diagram of an acoustic wave device having a single transducer providing input and output transduction processes and interacting with a fluid, including drive electronics and other electronics, in accordance with an alternative embodiment of the invention in which a single power measurement is employed.

An alternate embodiment of the proposed invention is depicted in FIG. 5. The figure depicts a one-port acoustic wave device 500, such as the well-known quartz-crystal microbalance by way of example, comprising at least a piezoelectric material with positive 510 and negative 515 polarity electrode arrays. The arrays consist of at least one conductive electrode of each polarity having any of the multitude of physical structures known to form a transducer. At least one of the electrodes is coupled to a driving electrical circuit 520 and power level detector 525. The power level detector 525 measures a single power level, which determines $P_{avg}$. The remainder of the previously-described methods function as described based on the measured $P_{avg}$. In the preferred embodiment, viscosity measurement is done by measuring deviation from $P_{avg}$. The system may also include other detection modules 530 (such as for phase, frequency, impedance and the like) for measuring viscosity by other known methods. The driving electrical circuit 520 may be any of a fixed frequency source, an oscillator designed to oscillate at the resonant frequency of the acoustic wave device, a variable frequency source designed to track a property of the acoustic wave device, or other excitation circuitry as may be devised to drive the acoustic wave device's transducer at a known amplitude and frequency.

Figure 6:
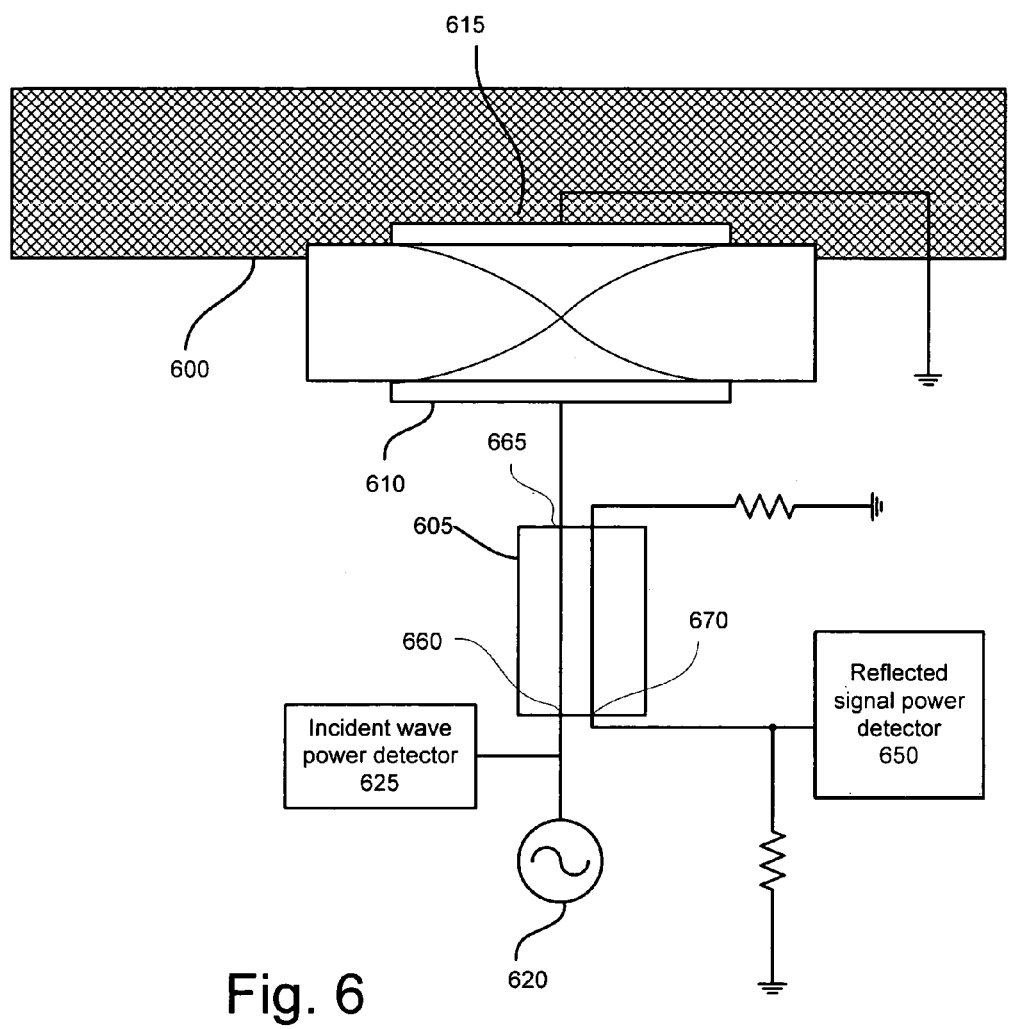
FIG. 6 depicts a simplified diagram of an acoustic wave device having a single transducer providing, input and output transduction processes and interacting with a fluid, including drive electronics and other electronics, in accordance with an alternative embodiment of the invention in which a directional coupler provides for input and output power level measurements.

Yet another embodiment of the proposed invention is depicted in FIG. 6, which shows a one-port acoustic wave device 600 with positive 61.0 and negative 615 electrode arrays coupled to a directional coupler 605. Driving circuitry 620 capable of providing harmonic signal power, and an incident wave power detector 625 are coupled to the incident port 660 of the directional coupler 605. The transducer formed by the positive 610 and negative 615 electrode arrays, is coupled to the transmission port 665 of the directional coupler 605 and a reflected signal power detector 650 is connected to the reflection port 670 of the directional coupler 605. Comparison of the incident and reflected power levels yields a reflection coefficient and thus an input impedance of the acoustic wave device while the incident power level defines $P_{avg}$. As in the case of the embodiment depicted in FIG. 5 the detection methods of the shear rate at which the viscosity measurement is carried out is derived from $P_{avg}$.

It will be clear to those skilled in the art that the physical structures, the calculations, process flow, and other detailed provided above are but one example of how to make the invention, and that one skilled in the art would be able to divide the provided functionality in many ways and circuit and transducer designs, given the flexible nature of electronics. While there has been provided a complete description of what is at present believed to be the best methods to practice the invention, the invention is clearly directed at covering such modifications and equivalents as will be clear to those skilled persons, and not limited to the logical block arrangement, algorithms, transducer designs, or other aspects of the description and drawings provided by way of none limiting example only.

What is claimed is:

1. A method for measuring viscosity of a fluid at a desired shear rate, utilizing an acoustic wave device having an input transducer and an output transducer, and having a known relationship between input power, output power, and an acoustic wave amplitude at a selected region between the input and output transducer, the acoustic wave device being coupled to the measured fluid, the method comprising the steps of:

i. selecting a desired shear rate, and an initial input power level as an estimated power level;

ii. applying a harmonic signal having the estimated power level to the input transducer to impart an acoustic wave of pre-selected amplitude at the selected region;

iii. using the acoustic wave device, measuring viscosity of the fluid to obtain a measured viscosity at the selected region;

iv. calculating an actual shear rate of the fluid at the selected region by using the viscosity measurements and the acoustic wave amplitude;

v. calculating the difference between the actual shear rate and the desired shear rate to produce a shear rate error;

vi. adjusting the estimated input power level to compensate for the shear rate error; and vii. using the adjusted estimated power level, repeating steps iii through vi until the shear rate error is within acceptable tolerance from the desired shear rate.

2. A method for measuring viscosity of a fluid at a desired shear rate as claimed in claim 1, wherein the step of selecting an input power level further comprises the step of estimating the input power level required to impart the desired shear rate to the fluid, and using the estimated power level in the step of applying a harmonic signal.

3. A method for measuring viscosity of a fluid at a desired shear rate as claimed in claim 2, wherein the step of estimating an input power level utilizes information relating to the fluid to be measured for estimating the acoustic wave amplitude.

4. A method for measuring viscosity of a fluid at a desired shear rate as claimed in claim 1, wherein in the step of selecting an initial power level, the estimated power level is being selected randomly.

5. A method for measuring viscosity of a fluid at a desired shear rate as claimed in claim 1, wherein in the step of selecting an initial power level, the estimated power level is selected to be about the mid point of the power range applicable to the acoustic wave device.

6. A method for measuring viscosity of a fluid at a desired shear rate as claimed in claim 1, wherein the step of measuring the viscosity is carried out by calculating power insertion loss of the signal transmitted between the input transducer the and output transducer.

7. A method for measuring viscosity of a fluid at a desired shear rate as claimed in claim 1, wherein the step of measuring the viscosity is carried out by measuring a phase shift of the signal transmitted between the input transducer the and output transducer.

8. A method for measuring viscosity of a fluid at a desired shear rate as claimed in claim 1, wherein the step of measuring the viscosity is carried out by a frequency change required to maintain a constant phase shift of the signal transmitted between the input transducer the and output transducer.

9. A method for measuring viscosity of a fluid at a desired shear rate as claimed in claim 1, wherein the step of measuring viscosity is carried out by measuring the change in the impedance of a transducer.

10. A method for measuring viscosity of a fluid at a desired shear rate as claimed in claim 1, wherein the step of calculating the actual shear rate of the sensor is carried out by the formula $\dot{\gamma}=\omega U/\delta$, where the applied signal has frequency, F, and $\omega=2\pi F$ is the radian frequency of the applied signal, U is the acoustic wave amplitude measured as a surface displacement, and $\delta$ is a penetration depth of the coupled evanescent acoustic wave into the fluid.

11. A method for measuring viscosity of a fluid at a desired shear rate as claimed in claim 10, wherein the step of calculating the actual shear rate of the sensor employs the formula for penetration depth of the acoustic wave into the fluid, $\delta=\sqrt{2\eta/\omega\rho}$, where $\omega$ is the radian frequency of the applied harmonic wave having frequency, F, and $\omega=2\pi F$, $\rho$ is the density of the sample liquid, and $\eta$ is the intrinsic viscosity (Pascal-seconds).

12. A method for measuring viscosity of a fluid at a desired shear rate as claimed in claim 11, wherein the step of calculating the penetration depth of the acoustic wave into the fluid, $\delta=\sqrt{2\eta/\omega\rho}$, density information is obtained from the response of the acoustic wave device itself.

13. A method for measuring viscosity of a fluid at a desired shear rate as claimed in claim 10, wherein the step of calculating the actual shear rate of the sensor relates the wave displacement, 'U', to the average acoustic wave power flow through the sensor, $P_{avg}$, as $U=C\sqrt{P_{avg}}$, where 'C' is a design parameter of the acoustic wave device.

14. A method for measuring viscosity of a fluid at a desired shear rate as claimed in claim 1, wherein the step of calculating the shear rate is carried out by assuming a correlation between the acoustic wave amplitude and the geometric average of the power inserted at the input transducer and the power sensed at the output transducer.

15. A method for measuring viscosity of a fluid at a desired shear rate as claimed in claim 1, wherein the selected region contains therewith the geometrical midpoint between the input transducer and output transducer respective geometries.

16. A method for measuring viscosity of a fluid at a desired shear rate as claimed in claim 1, wherein the step of adjusting the estimated input power level is carried out utilizing a PID algorithm.

17. A method for measuring viscosity of a fluid at a desired shear rate as claimed in claim 1, wherein the step of adjusting the estimated input power level is carried out by adjusting the input power level to obtain a complete cancellation of the error.

* * * * *